United States Patent
Akselrod-Ballin et al.

(10) Patent No.: US 10,223,610 B1
(45) Date of Patent: Mar. 5, 2019

(54) SYSTEM AND METHOD FOR DETECTION AND CLASSIFICATION OF FINDINGS IN IMAGES

(71) Applicant: International Business Machines Corporation, Armonk, NY (US)

(72) Inventors: Ayelet Akselrod-Ballin, Tel-Aviv (IL); Leonid Karlinsky, Haifa (IL)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 15/784,141

(22) Filed: Oct. 15, 2017

(51) Int. Cl.
*G06K 9/00* (2006.01)
*G06K 9/62* (2006.01)
(Continued)

(52) U.S. Cl.
CPC .......... *G06K 9/6218* (2013.01); *A61B 5/0042* (2013.01); *A61B 5/055* (2013.01);
(Continued)

(58) Field of Classification Search
CPC . G06T 7/162; G06T 7/194; G06T 7/11; G06T 7/174; G06T 7/0012; G06T 7/68; G06T 2207/10088; G06T 2207/10104; G06T 2207/10116; G06T 2207/10132; G06T 2207/20081; G06T 2207/20084; G06T 2207/30068; G06T 2207/30101; A61B 5/0042; A61B 5/055; A61B 5/7267; A61B 5/7485; A61B 6/032; A61B 6/037; A61B 6/501; A61B 6/502; A61B 8/0808; G06K 9/4671; G06K 9/74; G06K 9/6218; G06K 2209/051
See application file for complete search history.

(56) References Cited

U.S. PATENT DOCUMENTS

2017/0277977 A1* 9/2017 Kitamura ............. G06K 9/6267
2018/0060648 A1* 3/2018 Yoo ..................... G06K 9/00228
(Continued)

OTHER PUBLICATIONS

Krizhevsky et al., "ImageNet Classification with Deep Convolutional Neural Networks", NIPS'12 Proceedings of the 25th International Conference on Neural Information Processing Systems, Dec. 2012, pp. 1097-1105.
(Continued)

*Primary Examiner* — Shefali D Goradia
(74) *Attorney, Agent, or Firm* — G.E. Ehrlich

(57) ABSTRACT

A system for detection and classification of findings in an image, comprising at least one hardware processor configured to: receive the image; process the image by a plurality of convolutional and pooling layers of a neural network to produce a plurality of feature maps; process one of the feature maps by some of the layers and another plurality of layers to produce a plurality of region proposals; produce a plurality of region of interest (ROI) pools by using a plurality of pooling layers to downsample the plurality of region proposals with each one of the plurality of feature maps; process the plurality of ROI pools by at least one concatenation layer to produce a combined ROI pool; process the combined ROI pool by a classification network comprising some other of the convolutional and pooling layers to produce one or more classifications; and output the one or more classifications.

20 Claims, 8 Drawing Sheets

(51) Int. Cl.
| | |
|---|---|
| *G06T 7/11* | (2017.01) |
| *G06T 7/162* | (2017.01) |
| *G06T 7/194* | (2017.01) |
| *G06T 7/174* | (2017.01) |
| *G06K 9/74* | (2006.01) |
| *G06K 9/46* | (2006.01) |
| *A61B 5/00* | (2006.01) |
| *A61B 5/055* | (2006.01) |
| *A61B 6/03* | (2006.01) |
| *A61B 6/00* | (2006.01) |
| *A61B 8/08* | (2006.01) |
| *G06T 7/00* | (2017.01) |
| *G06T 7/68* | (2017.01) |

(52) U.S. Cl.
CPC .......... *A61B 5/7267* (2013.01); *A61B 5/7485* (2013.01); *A61B 6/032* (2013.01); *A61B 6/037* (2013.01); *A61B 6/501* (2013.01); *A61B 6/502* (2013.01); *A61B 8/0808* (2013.01); *G06K 9/4671* (2013.01); *G06K 9/74* (2013.01); *G06T 7/0012* (2013.01); *G06T 7/11* (2017.01); *G06T 7/162* (2017.01); *G06T 7/174* (2017.01); *G06T 7/194* (2017.01); *G06K 2209/051* (2013.01); *G06T 7/68* (2017.01); *G06T 2207/10088* (2013.01); *G06T 2207/10104* (2013.01); *G06T 2207/10116* (2013.01); *G06T 2207/10132* (2013.01); *G06T 2207/20081* (2013.01); *G06T 2207/20084* (2013.01); *G06T 2207/30068* (2013.01); *G06T 2207/30101* (2013.01)

(56) References Cited

U.S. PATENT DOCUMENTS

| | | | | |
|---|---|---|---|---|
| 2018/0108137 | A1* | 4/2018 | Price | G06T 7/0081 |
| 2018/0137647 | A1* | 5/2018 | Li | G06K 9/4671 |
| 2018/0259608 | A1* | 9/2018 | Golden | G01R 33/5608 |

OTHER PUBLICATIONS

Giger et al., "Breast image analysis for risk assessment, detection, diagnosis, and treatment of cancer", Annual of Review Biomedical Engineering, 2013, pp. 327-357.

Oliver et al., "A review of automatic mass detection and segmentation in mammographic images", Med Image Anal., Apr. 2010, vol. 12, Issue 2, pp. 87-110.

Carneiro et al., "Unregistered Multiview Mammogram Analysis with Pre-trained Deep Learning Models", Medical Image Computing and Computer-Assisted Intervention—MICCAI 2015, pp. 652-660.

Arevalo et al., "Representation learning for mammography mass lesion classification with convolutional neural networks", Comput Methods Programs Biomed, Apr. 2016, vol. 127, pp. 248-257.

Dhungel et al., "Automated Mass Detection from Mammograms using Deep Learning and Random Forest", DICTA 2015.

Girshick et al., "Rich feature hierarchies for accurate object detection and semantic segmentation", IEEE Conference on Computer Vision and Pattern Recognition, Jun. 2014, pp. 580-587.

Ren et al., "Faster R-CNN: Towards Real-Time Object Detection with Region Proposal Networks", Advances in Neural Information Processing Systems 28 (NIPS), 2015.

Bekker et al., "A multi-view deep learning architecture for classification of breast microcalcifications", IEEE 13th International Symposium on Biomedical Imaging (ISBI), Apr. 2016, pp. 726-730.

Amit et al., "Automatic Dual-View Mass Detection in Full-Field Digital Mammograms", Medical Image Computing and Computer-Assisted Intervention (MICCAI), 2015, pp. 44-52.

Nishikawa, "Current status and future directions of computer-aided diagnosis in mammography", Computerized Medical Imaging and Graphics, Jun.-Jul. 2007, vol. 31, Issues 4-5, pp. 224-235.

Akselrod-Ballin et al., "A Region Based Convolutional Network for Tumor Detection and Classification in Breast Mammography", Deep Learning and Data Labeling for Medical Applications, 2016, pp. 197-205.

* cited by examiner

SYSTEM AND METHOD FOR DETECTION AND CLASSIFICATION OF FINDINGS IN IMAGES

BACKGROUND

The present invention, in some embodiments thereof, relates to a system and method for detection and classification of multiple findings in images and, more specifically, but not exclusively, to an automatic system and method for detection and classification of multiple findings in medical images.

In medical image analysis an expert radiologist typically examines one or more images, for example images captured by computerized tomography, ultrasound or mammography, and analyses the one or more images to detect and classify potential abnormalities. Detection and classification of abnormalities is complicated by factors such as there being multiple categories of abnormalities and variability in appearance of abnormalities, such as size, shape, boundaries and intensities, as well as factors such varying viewing conditions and anatomical tissue being non-rigid. Examples of abnormality categories are lesions, calcifications, microcalcifications and tumors.

Image classification is the task of taking an input image and outputting a class or one or more features (a cat, a dog, etc.) or a probability of classes (features) that best describes the image. The term Deep Learning (DL) is used to refer to methods aimed at learning feature hierarchies, with features from higher levels of a hierarchy formed by composition of lower lever features. For example, in computer vision, a feature may be a certain visible object or a certain visible characteristic of an object. Examples of low level features are a color, a texture, an edge and a curve. Examples of high level features are a dog, a cat, a car and a person. In an example of hierarchical features in computer vision, a dog may be identified by a composition of one or more paws, a body, a tail and a head. In turn, a head may be identified by a composition of one or two eyes, one or two ears and a snout. An ear may be identified by a certain shape of an outlining edge. Automatically learning features at multiple levels of abstraction allows a system to learn complex functions mapping an input image to an output classification directly from data, without depending completely on human-crafted features.

As appropriate technologies develop, computer vision techniques are employed to assist radiologists in detection and classification of abnormalities in medical images. The term neural network is commonly used to describe a computer system modeled on the human brain and nervous system. A neural network usually involves a large number of processing objects operating in parallel and arranged and connected in layers (or tiers). A first layer receives raw input information (one or more input records), analogous to optic nerves in human visual processing. Each successive layer receives an output from one or more layers preceding it, rather than from the raw input—analogous to neurons further from the optic nerve receiving signals from neurons closer to the optic nerve. A last layer produces an output of the neural network, typically one or more classes classifying the raw input information. In computer vision the raw input information is one or more images, and the output is one or more feature classifications detected in the image. In recent years, deep neural networks (DNN) are used for image recognition, specifically convolutional neural networks (CNN). The term "deep" refers to the amount of layers in such a neural network. A CNN in computer vision is a neural network having a series of convolutional layers which apply one or more convolutional filters to a digital representation of an input image. For each sub-region of the image, each of the plurality of convolutional layers performs a set of mathematical operations to produce a single value in an output feature map, representing one or more spatial features in the image. The CNN is able to perform image classification by looking for low level features such as edges and curves, and then building up to more abstract concepts through the series of convolutional layers.

Such technologies have been applied successfully in a plurality of fields, including for classifying lesions and calcifications in breast mammography images. However, commonly used methods perform either feature classification or detection localization (determining coordinates of the feature with reference to the input image) but not both.

SUMMARY

It is an object of the present invention to provide a system and method for detection and classification of multiple findings in images and, more specifically, but not exclusively, an automatic system and method for detection and classification of multiple findings in medical images.

The foregoing and other objects are achieved by the features of the independent claims. Further implementation forms are apparent from the dependent claims, the description and the figures.

According to a first aspect of the invention, a system for detection and classification of findings in an image, comprises at least one hardware processor configured to: receive the image; process the image by a first plurality of convolutional and pooling layers of a neural network to produce a plurality of feature maps, each one of the plurality of feature maps comprising a plurality of location coordinates related to the image; process one of the plurality of feature maps by some of the first plurality of convolutional and pooling layers, a second plurality of convolutional and pooling layers and a first plurality of fully connected layers of the neural network to produce a plurality of region proposals; produce a plurality of region of interest (ROI) pools by using a third plurality of pooling layers of the neural network to downsample the plurality of region proposals with each one of the plurality of feature maps; process the plurality of ROI pools by at least one pool concatenation layer of the neural network to produce a combined ROI pool; process the combined ROI pool by a classification network comprising some other of the first plurality of convolutional and pooling layers to produce one or more classifications; and output the one or more classifications. Producing classifications using a plurality of ROI pools created using a plurality of feature maps allows considering features from a variety of resolutions, increasing the accuracy of classification.

According to a second aspect of the invention, a method for detection and classification of findings in an image, comprises: receiving the image; processing the image by a first plurality of convolutional and pooling layers of a neural network to produce a plurality of feature maps, each one of the plurality of feature maps comprising a plurality of location coordinates related to the image; processing one of the plurality of feature maps by some of the first plurality of convolutional and pooling layers, a second plurality of convolutional and pooling layers and a first plurality of fully connected layers of the neural network to produce a plurality of region proposals; producing a plurality of region of interest (ROI) pools by using a third plurality of pooling layers of the neural network to downsample the plurality of region proposals with each one of the plurality of feature maps; processing the plurality of ROI pools by at least one pool concatenation layer of the neural network to produce a combined ROI pool; processing the combined ROI pool by a classification network comprising some other of the first plurality of convolutional and pooling layers to produce one or more classifications; and outputting the one or more classifications.

According to a third aspect of the invention, a system for detection and classification of findings in an image, comprises at least one hardware processor configured to: receive the image; receive a plurality of values of a plurality of attributes related to the image; process the plurality of values by a first plurality of fully connected layers of a neural network to produce a plurality of processed values; integrate the plurality of processed values into a plurality of layers of the neural network; process the image by a first plurality of convolutional and pooling layers of a neural network to produce at least one feature map, each one of the at least one feature map comprising a plurality of location coordinates related to the image; process one of the at least one feature map by some of the first plurality of convolutional and pooling layers, a second plurality of convolutional and pooling layers and a second plurality of fully connected layers of the neural network to produce a plurality of region proposals; produce a plurality of region of interest (ROI) pools by using a third plurality of pooling layers of the neural network to downsample the plurality of region proposals with each one of the at least one feature map; process the plurality of ROI pools by at least one pool concatenation layer to produce a combined ROI pool; process the combined ROI pool by a classification network comprising some other of the first plurality of convolutional and pooling layers to produce one or more classifications; and output the one or more classifications. Incorporating additional information about the image collected from sources other than the system adds accuracy to the resulting classifications.

With reference to the first and second aspects, in a first possible implementation of the first and second aspects of the present invention the first plurality of convolutional and pooling layers comprises a plurality of layer blocks, each layer block comprising a sequence of convolutional and pooling layers. The plurality of layer blocks are connected in a topology selected from a group consisting of a linear graph and a directed acyclic graph. The present invention does not limit the topology of the neural network.

With reference to the first and second aspects, or the first implementation of the first and second aspects, in a second possible implementation of the first and second aspects of the present invention the plurality of layer blocks of the first plurality of convolutional and pooling layers are connected linearly. The first plurality of convolutional and pooling layers comprises a first layer block comprising a first sequence of layers consisting of: an input layer, followed by a first sequence of convolutional and rectified linear unit layers, followed by a first pooling layer, followed by a second layer block comprising a second sequence of convolutional and rectified linear unit layers, followed by a second pooling layer, followed by a third layer block comprising a third sequence of convolutional and rectified linear unit layers, followed by a third pooling layer, followed by a fourth layer block comprising a fourth sequence of convolutional and rectified linear unit layers, followed by a fourth pooling layer, and followed by a fifth layer block comprising a fifth sequence of convolutional and rectified linear unit layers. An output of the third sequence of convolutional and rectified linear unit layers is connected to a first normalized convolutional layer; an output of the fourth sequence of convolutional and rectified linear unit layers is connected to a second normalized convolutional layer; a first of the plurality of feature maps is produced by the first normalized convolutional layer; a second of the plurality of feature maps is produced by the second normalized convolutional layer; a third of the plurality of feature maps is produced by the fifth sequence of convolutional and rectified linear unit layers; and one of the plurality of feature maps is the third of the plurality of feature maps. Extracting feature maps from different depths of the neural network may improve accuracy of classifications. Optionally, each one of the plurality of region proposals comprises a boundary box, an object likelihood score and a non-object likelihood score. Optionally, the third plurality of layers comprises a second sequence of layers consisting of: an ROI pooling layer, followed by a fifth pooling layer, followed by a fully connected layer and followed by a pooling reshaping layer. Optionally, the classification network further comprises some of the first plurality of fully connected layers, a fourth plurality of fully connected layers, at least one bounding box regressor layer and one or more loss layers. Sharing fully connected layers between a network for producing ROI proposals and the classification network helps expedite learning processes and may improve accuracy of classifications.

With reference to the first and second aspects, in a third possible implementation of the first and second aspects of the present invention, when the image is captured by a mammography of a breast the method further comprises after receiving the image: removing background and pectoral muscle from the image to produce a breast tissue image; receiving a plurality of other images; producing a plurality of visual attributes; and dividing the breast tissue image into a plurality of overlapping sub-images. Producing the plurality of visual attributes comprises: by: extracting Fibroglandular tissue from the breast tissue image and the plurality of other images; extracting at least one saliency map of the breast tissue image and the plurality of other images; and processing the breast tissue image and the plurality of other images to produce a plurality of vessel identifications. After producing the one or more classifications and before outputting the one or more classifications the method further comprises: projecting one or more bounding boxes of the one or more classifications on the image.

With reference to the first and second aspects, in a fourth possible implementation of the first and second aspects of the present invention, the method further comprises after producing the one or more classifications and before outputting the one or more classifications: clustering the one or more classifications according to redundant and overlapping bounding boxes to produce a one or more clustered classifications; and projecting one or more bounding boxes of the clustered classifications on the image. Projecting bounding boxes on the input image may assist medical practitioners using the results of classification.

With reference to the first and second aspects, in a fifth possible implementation of the first and second aspects of the present invention the at least one hardware processor is further configured to: execute an electronic record management (ERM) system for storing a plurality of medical records comprising a plurality of medical images; store the image in the ERM system; retrieve the medical image from the ERM system before processing the image by the first plurality of convolutional and pooling layers; and store the one or more classifications in the ERM system. Optionally, each one of the one or more classifications comprises a bounding box, a class and a probability score of the class at the bounding box; the at least one hardware processor is further configured to issue an alert upon determining the class of at least one of the one or more classifications is a member of a predetermined set of abnormal classes and the probability score of the at least one classification is greater than a threshold score value. ERM systems are used in some medical environments. Integrating with an ERM system improves usability of the present invention in a medical environment. Optionally, the ERM system comprises a database. Optionally, the ERM stores the image in a format compliant with Digital Imaging and Communications in Medicine (DICOM).

With reference to the first and second aspects, in a sixth possible implementation of the first and second aspects of the present invention the image is received by the at least one hardware processor via a network communications protocol compliant with DICOM. Complying with a common standard such as DICOM improves usability of the present invention in existing medical environments.

With reference to the third aspect, in a first possible implementation of the third aspect of the present invention the plurality of processed values is integrated into the plurality of layers by processing the plurality of processed values and the plurality of ROI pools by the least one pool concatenation layer to produce the combined ROI pool. Incorporating additional information about the image collected from sources other than the system into the combined ROI pool is one possible method of adding accuracy to the resulting classifications.

With reference to the third aspect, in a second possible implementation of the third aspect of the present invention the plurality of processed values is integrated into the plurality of layers by using the plurality of processed values as modulators for a plurality of convolutional kernels of the first plurality of convolutional and pooling layers before processing the image to produce the plurality of feature maps. Using the additional information about the image collected from sources other than the system as modulators of convolutional kernels when producing the plurality of feature maps is another possible method of adding accuracy to the resulting classifications.

With reference to the third aspect, in a third possible implementation of the third aspect of the present invention the image is a medical image. Optionally, the medical image is captured by a mammography of a breast or by a method selected from a group consisting of: a computerized tomography of a brain, a magnetic resonance imaging of a brain, an ultrasound of a brain, a positron emission tomography of a brain and an X-ray radiography of a brain. When the image is captured by a mammography of a breast, optionally the plurality of attributes are selected from a group consisting of: a clinical record of a patient, a positive mask corresponding with an anatomical feature, a negative mask corresponding with an anatomical feature, a computed visual attribute, a density, a symmetry property, an additional view of the image, and a feature detected in another image. Optionally, the positive mask corresponds to Axilla tissue or Fibroglandular tissue. Optionally, the negative mask corresponds to a blood vessel. When the image is an image of a brain, optionally the positive mask corresponds to white matter.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
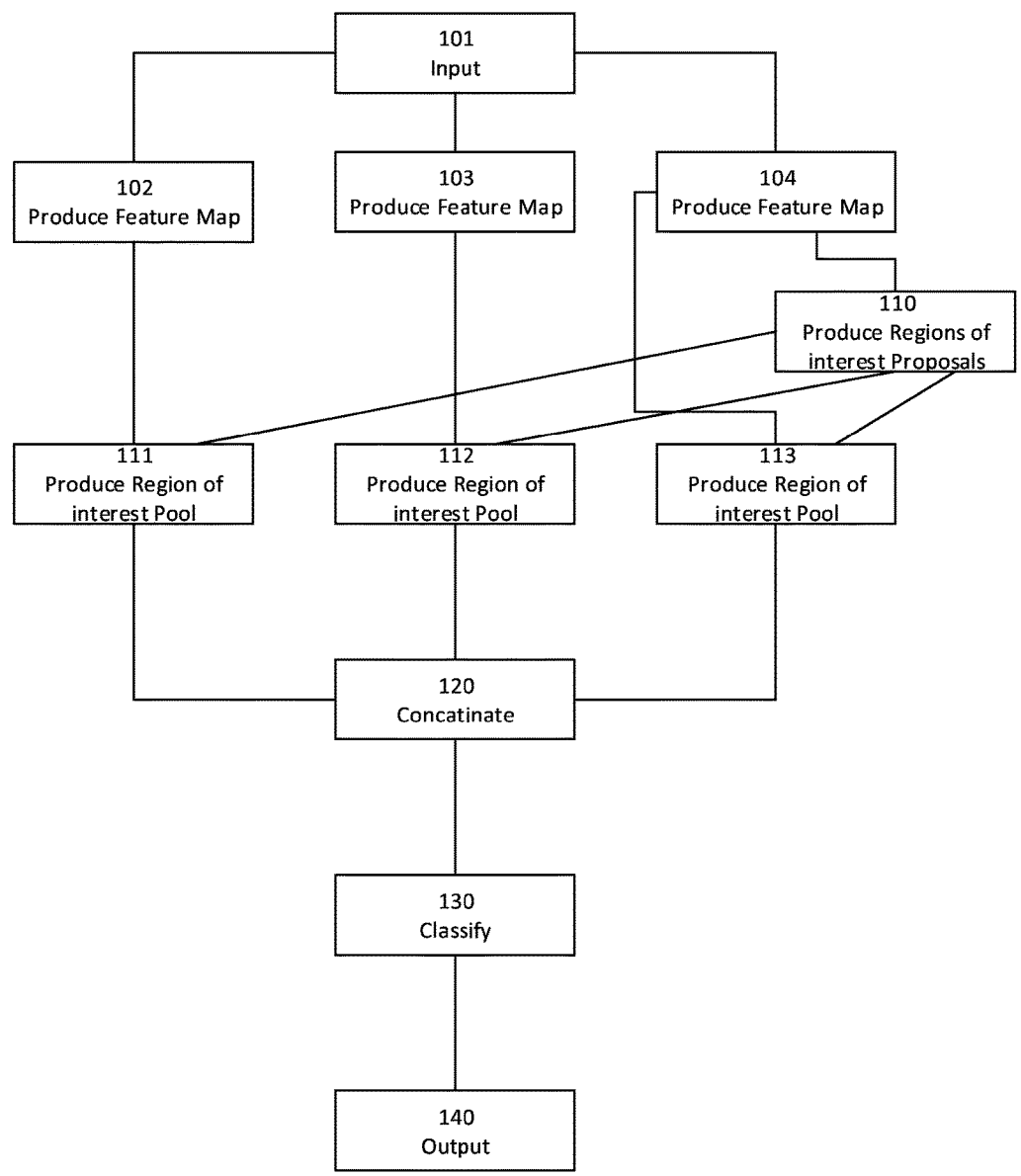
FIG. 1 is a flowchart schematically representing an optional flow of operations for processing an image, according to some embodiments of the present invention.

The following description details the use of the present invention, in some embodiments thereof, for detection and classification of abnormal findings in breast tissue; however the present invention may be used with other medical images or with non-medical images. An example of other medical images is images of brain tissue. An example of non-medical images is architectural structures such as a building's foundations, walls etc.

A key feature of a neural network is the neural network's ability to learn, by comparing the computed classification of an input record with a known actual classification of the input record. Iteratively, for a plurality of iterations, errors from one classification of an input record are used to modify algorithms in the neural network when processing the input record another time. A typical computation in a neural network involves summing a plurality of products between an input value and an associated weight, and mapping the resulting sum to an output value. Training a neural network refers to a process of adjusting a plurality of weights of the plurality of layers of the neural network according to error terms between a computed class and a known class of an input record, such that in a next iteration the output class will be closer to the known class than in a previous iteration.

In a typical neural network having a plurality of layers, the final layer is an output layer, having one node for each class the neural network can identify. For example, in computer vision, the final layer typically has one node for each feature the neural network can identify and for which the neural network can output an identification. A single sweep forward of an input record through the neural network, starting from the input layer to the output layer, through a plurality of intermediate layers, results in an assignment of a value to each output node, and the input record is assigned to whichever class's node has the highest value. In computer vision, the input record is an image, and the output comprises one or more possible features detected in the image. In an iterative training process, a plurality of input records may be presented to the neural network one at a time, and the weights associated with the input records may be adjusted each time. After all records are presented, the process may start over again. During this training process, the neural network learns by adjusting the weights so as to be able to predict the correct class label of input records. Use of the Faster Region based CNN (Faster R-CNN), as described in Ren S., He K., Girshick R., & Sun J. "Faster R-CNN: Towards Real Time Object Detection with Region Proposal Networks", Advances in Neural Information Processing Systems 28 (NIPS 2015), has improved detection speeds and detection quality compared to previously used methods such as Region based CNN (R-CNN). In computer vision, Faster C-RNN uses two modules: a region proposal module for generating a plurality if region proposals, that is regions in the input image likely to contain features, using low level cues such as color and texture, and a region classification module for computing a plurality of CNN features and classifying the plurality of computed features into object categories (classes). The two modules are CNNs, sharing a plurality of shared layers and weights. Faster R-CNN introduced end-to-end joint training of both the region proposal module and the region classification module.

The present invention, in some embodiments thereof, allows adapting Faster R-CNN general computer vision deep learning algorithms to a specific problem domain, for example a specific medical problem domain such as abnormalities in breast images or brain images, by using low level feature information in generating a plurality of region proposals and by introducing to a plurality of layers in the CNN anatomical information, clinical attributes obtained from sources other than an input image, and visual attributes obtained from other images or from other processing of the input image. Examples of anatomical information are a positive mask corresponding to an Axilla or Fibrograndular tissue in a breast, a positive mask corresponding to white matter in a brain and a negative mask corresponding to blood vessels in a breast. Examples of a clinical attribute are a patient's age and a medical history of a patient's family. Examples of visual attributes are a length of a lesion and a lesion's intensity. Visual attributes may include features produced by processing other images captured by a different model such as an ultrasound image. Some of the anatomical information and attributes might be lost by a fully automatic learning process. The present invention, in some embodiments thereof, provides the anatomical information and attributes as additional external normalized inputs to strategic layers of the neural network while taking care to normalize intermediate deep features to be combined with the external inputs, allowing incorporation of prior knowledge and expertise that might otherwise be lost. Adapting general Faster R-CNN algorithms to a specific problem domain and incorporating prior knowledge and expertise that might otherwise be lost increases the accuracy of detection and reduces the amount of false positive and false negative identification of features compared to using general computer vision deep learning algorithms. The present invention, in some embodiments thereof, automatically separates images with one or more abnormal features from images with no abnormal features, allowing a radiologist to focus on diagnosis of patients having abnormal features. Focusing on patients having abnormal features may expedite diagnosis and reduce delays in diagnosis in environments suffering from insufficient radiology expertise due to distance from an expert clinic or financial limitations. In addition, more accurate classification of abnormalities may reduce the need to perform a biopsy on a patient, reducing cost of medical treatments, as well as patient discomfort and health risks following an invasive medical procedure.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used henceforth, the term "network" means "neural network".

In some embodiments of the present invention a system for processing an input image comprises at least one hardware processor configured to execute one or more layers of a neural network.

In order to process an image, such a system implements in some embodiments of the present invention the following method.

Reference is now made to FIG. 1, showing a flowchart schematically representing an optional flow of operations for processing an image, according to some embodiments of the present invention. In such embodiments, the system classifies a combined region of interest pool, produced by combining a plurality of pools of regions of interest, each produced by pooling a plurality of region of interest proposals with one of a plurality of feature maps, according to one or more boundary boxes associated with the plurality of region of interest proposals. A boundary box is a set of locations related to the input image defining the locality and bounds of a feature or an object in the input image. The plurality of feature maps is produced at a plurality of depths of the neural network. The term depth of a neural network refers to an amount of layers used for processing. As the amount of layers used in processing increases, the output is considered produced deeper in the neural network. Optionally, the system receives in 101 the input image. Optionally, the input image is a medical image, for example an image of a breast or an image of a brain. Optionally, the input image is captured by mammography. Optionally, the input image is captured by Computerized Tomography. Optionally, the image is captured by a method selected from a group including: magnetic resonance imaging, ultrasound, positron emission tomography and X-ray radiography. Next, the input image is processed by a first plurality convolution and pooling layers of the neural network to produce in 102, 103 and 104 a plurality of feature maps from a plurality of depths of the neural network. Optionally, each of the plurality of feature maps comprises a plurality of location coordinates related to the image. A feature may be a low level feature such as an edge or a curve. A feature may be a higher level feature such as a lesion or calcification. Two or more feature maps produced at different depths may relate to different sub images of the input image, may be processed at different resolutions and using different amounts of processing. As a result, two or more feature maps produced at different depths may have different features. Optionally some of the plurality of feature maps include one or more low level features. Optionally some other of the plurality of feature maps include one or more higher level features. Using a plurality of feature maps from a plurality of depths of the neural networks allows introducing multiscale context into a classification process, increasing accuracy of classification.

Figure 2:
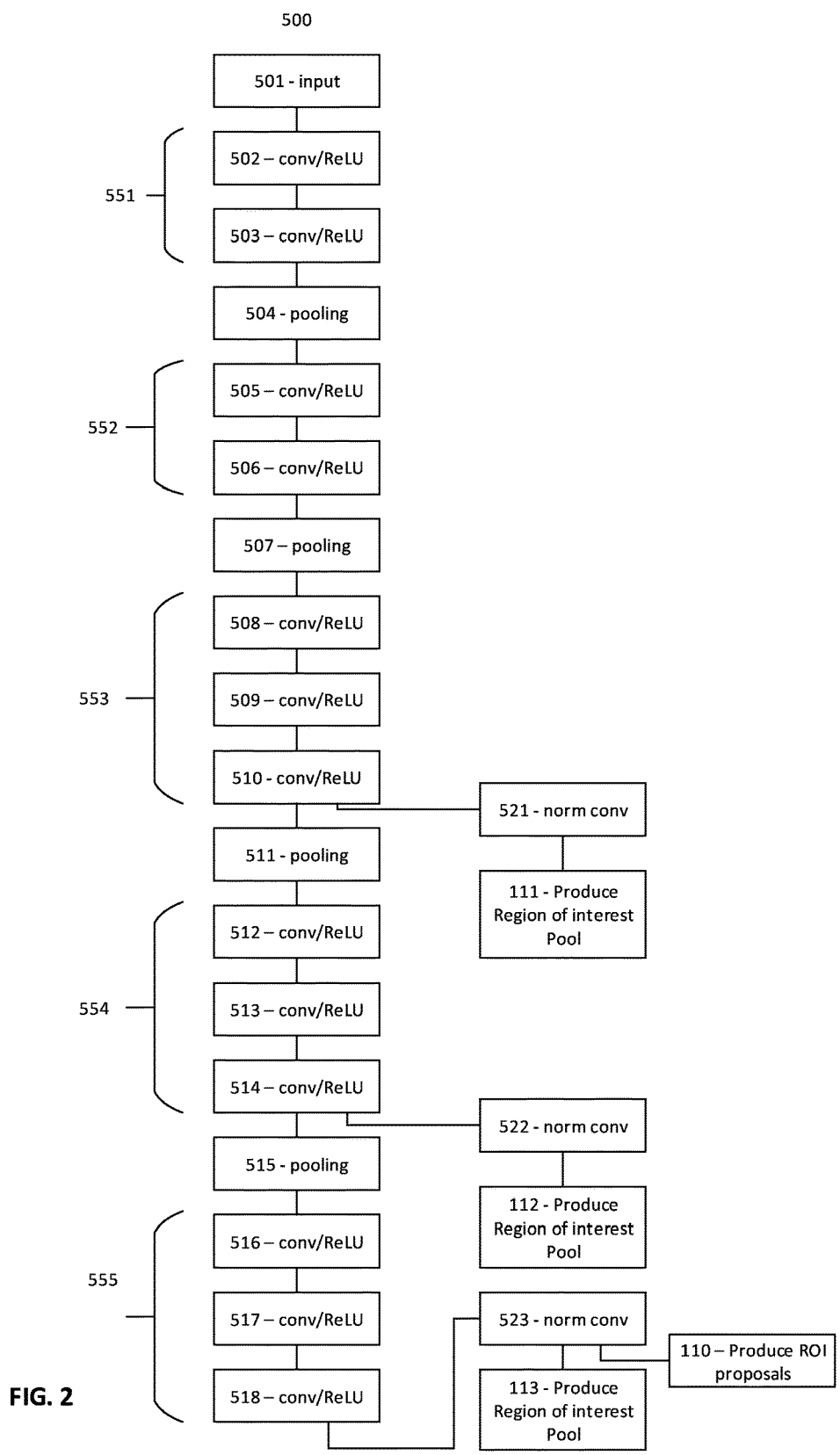
FIG. 2 is a schematic block diagram of an exemplary neural network for extracting feature from an image, according to some embodiments of the present invention.

Reference is now also made to FIG. 2, showing a schematic block diagram 500 of an exemplary neural network for extracting features from an image in 102, 103 and 104, according to some embodiments of the present invention. In such embodiments, the neural network comprises a plurality of connected layer blocks 551, 552, 553, 554 and 555. Each layer block comprises a sequence of layers. The plurality of layer blocks may be connected in a linear topology. The plurality of layer blocks may be connected in another topology, for example a directed acyclic graph.

Optionally, a plurality of sequences (layer blocks) of convolutional and rectified linear units layers are used to extract from the image multiple feature maps. Each of the plurality of sequences may extract one of an identified set of features. For example, when processing an image of a breast, one plurality may extract one or more masses and another plurality may extract one or more non-benign calcifications. Optionally, following an input layer 501 for receiving the input image, the neural network comprises a first sequence 551 of convolutional and rectified linear unit (ReLU) layers. A convolutional layer is a layer to filter an input image and detect a pattern in the image, by convolving around the input image and computing high values, also known as activating, when the pattern is in the input image. An ReLU layer is a layer employing an element wise activation (rectifier) function such as f(x)=MAX(0, x). An ReLU layer may be used to introduce non-linearities into a model. Optionally, following plurality 551, a pooling layer 504 is connected. A pooling layer may be used to reduce a feature map's dimensionality, in order to decrease processing time. An example of a pooling algorithm used by a pooling layer is max pooling. Max pooling extracts a plurality of subregions of a feature map, keeps a maximum value of each of the plurality of subregions and discards all other values of the feature map. Optionally, pooling layer 504 is connected to a second sequence 552 of convolutional and ReLU layers 505 and 506. Optionally, sequence 552 is followed by a second pooling layer 507, next followed by a third sequence 553 of convolutional and ReLU layers 508, 509 and 510. In some embodiments of the present invention, an output of convolutional and ReLU layers 510 is connected to a normalized convolutional layer 521 for normalizing values for use in future layers receiving input from one or more layers other than layer 521, and an output of layer 521 is connected to an input of a network 111 for producing a first pool of regions of interest. In some embodiments a plurality of feature maps are produced. In such embodiments, an output of layer 510 is attached to a third pooling layer 511, followed by a fourth sequence 554 of convolutional and ReLU layers 512, 513 and 514. Optionally, an output of layers 514 is connected to an input of normalized convolutional layer 522, and an output of layer 522 is connected to an input of a network 112 for producing a second pool of regions of interest. Optionally, an output of layers an output of layer 514 is attached to a fourth pooling layer 515, followed by a fifth sequence 555 of convolutional and ReLU layers 516, 517 and 518. Optionally, an output of layers 518 is connected to an input of normalized convolutional layer 523, and an output of layer 523 is connected to an input of a network 112 for producing a third pool of regions of interest. In addition, an output of layer 523 is connected to an input of a network 110 for producing a plurality of region of interest proposals.

Reference is now made again to FIG. 1. In some embodiments of the present invention, one of the plurality of feature maps, for example a feature map produced in 104, is processed by a region proposal network comprising a plurality of layers of the neural network to produce a plurality of region of interest proposals. Optionally, the region proposal network shares some convolutional and pooling layers with the network used to compute the plurality of feature maps, such that the region proposal network comprises some of the first plurality of convolutional and pooling layers, as well as a second plurality of convolutional and pooling layers and a first plurality of fully connected layers of the neural network. A fully connected layer takes an input from a convolutional or ReLU or pooling layer preceding it and outputs a plurality of values, each representing a probability of a certain class selected from a predefined set of classes. For example, in some embodiments a fully connected is configured to consider what high level features most strongly correlate to a particular class and has particular weights so that computing products between the fully connected layer's weights and the input received from the preceding layer, produces a correct probability for the each of the predefined set of classes.

Figure 3:
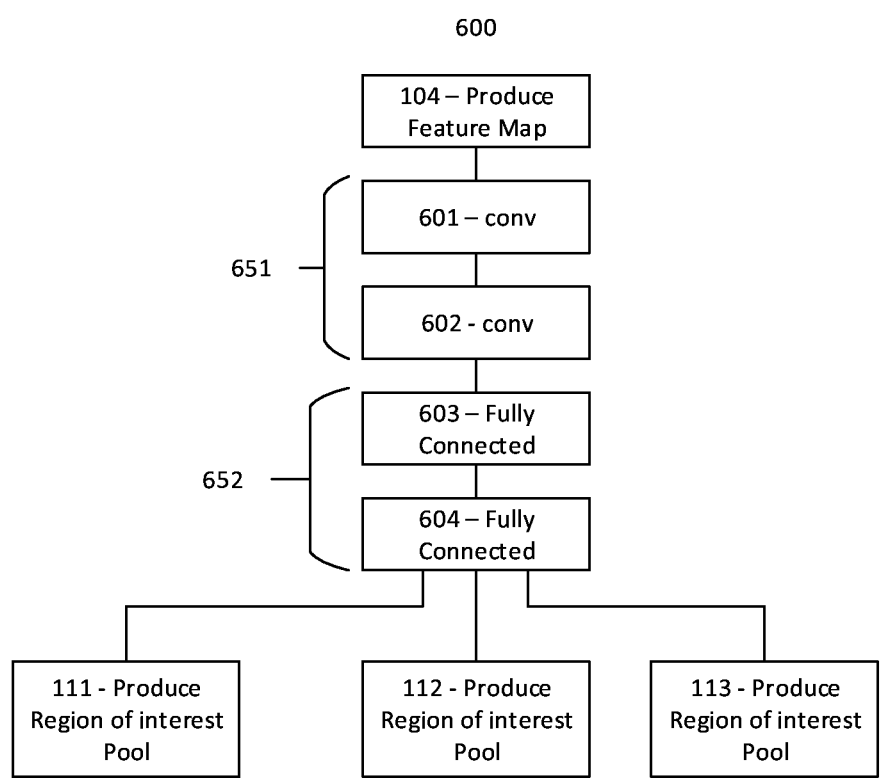
FIG. 3 is a schematic block diagram of an exemplary neural network for region of interest proposals, according to some embodiments of the present invention.

Reference is now also made to FIG. 3, showing a schematic block diagram 600 of an exemplary neural network for producing region of interest proposals in 110, according to some embodiments of the present invention. In such embodiments, following production of a feature map in 104, a sequence 651 of convolutional layers 601 and 602 are connected to a sequence 652 of fully connected layers 603 and 604. Optionally, layer 601 classifies a plurality of anchors to objects and background. Optionally layer 602 performs linear regression to improve an accuracy of the plurality of anchors produced by layer 601. Processing the feature map by layers 601, 602, 603 and 604 optionally produces a plurality of region of interest proposals. Optionally, each of the region of interest proposals comprises a boundary box, an object likelihood score and a non-object likelihood score. A boundary box is a set of locations related to the input image defining the locality and bounds of a feature or an object in the input image. An object likelihood score is a value denoting a probability that an object is in the image within the boundary box. A non-object likelihood score is a value denoting a probability that an object is not in the image within the boundary box.

Reference is now made again to FIG. 1. The plurality of regions proposals produced in 110 is optionally processed in 111, 112 and 113 together with each one of the plurality of feature maps produced in 102, 103 and 104 respectively, to produce a plurality of region of interest pools.

Figure 4:
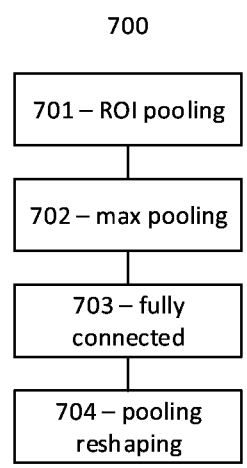
FIG. 4 is a schematic block diagram of an exemplary neural network for producing a pool of regions of interest, according to some embodiments of the present invention.

Reference is now made to FIG. 4, showing a schematic block diagram 700 of an exemplary neural network for producing a pool of regions of interest in each of 111, 112 and 113, according to some embodiments of the present invention. In such embodiments, a Region Of Interest (ROI) pooling layer 701 is followed by a pooling layer, for example a max pooling layer, 702, followed by a fully connected layer 703, followed by a pooling reshaping layer 704. Layers 701, 702 and 703 optionally downsample the regions of interest proposals with one feature map of the plurality of feature maps. Downsampling reduces the region of interest proposals' dimensionality for computational efficiency. Max pooling uses the maximum value from each of a cluster of neurons at a prior layer. ROI pooling is a variant of max pooling, in which output size is fixed. A pooling reshaping layer transforms an input of a previous layer to predefined output dimensions, for example the input image's dimensions.

Reference is now made again to FIG. 1. A plurality of pools of regions of interest produced in 111, 112 and 113 is optionally processed in 120 by a pool concatenation layer to produce a combined region of interest pool. Next, in 130 the combined region of interest is optionally processed by a classification network to produce one or more classifications, and the one or more classifications are optionally outputted in 140. Optionally, a classification comprises a class, selected from a predefined set of classes, or a probability score of each of one or more classes selected from the predefined set of classes, that best describes the image, and for each one class of the one or more classes a bounding box relative to the image and associated with the one class. Optionally, the classification network comprises a plurality of classification fully connected layers. Optionally the classification network shares fully connected layers with the region proposal network, such that the classification network comprises some of the first plurality of fully connected layers of the region proposal network, as well as another plurality of fully connected layers. Some region of interest proposals in the plurality of region of interest proposals might not fully coincide with one or more regions indicated by the one or more feature maps produced in 102, 103 and 104. Optionally, the classification network comprises at least one bounding box regressor layer, to give a better estimate of object position by using features generated by deep layers of the neural network. Optionally, the classification network comprises one or more loss layers. A loss layer specifies how network training penalizes a deviation between a predicted class and a true class.

To improve the accuracy of classifications, in some embodiments, the input image is pre-processed before being processed by the neural network in order to remove values in the image that might interfere with detection and classification of features in the image. In addition, pre-processing allows producing anatomical information and attributes that might be lost by a fully automatic learning process. In addition, in some embodiments of the present invention, outputting the one or more classifications includes projecting the one or more classifications on the input image. To pre-process and post process the input image, the system optionally implements the following method.

Figure 5:
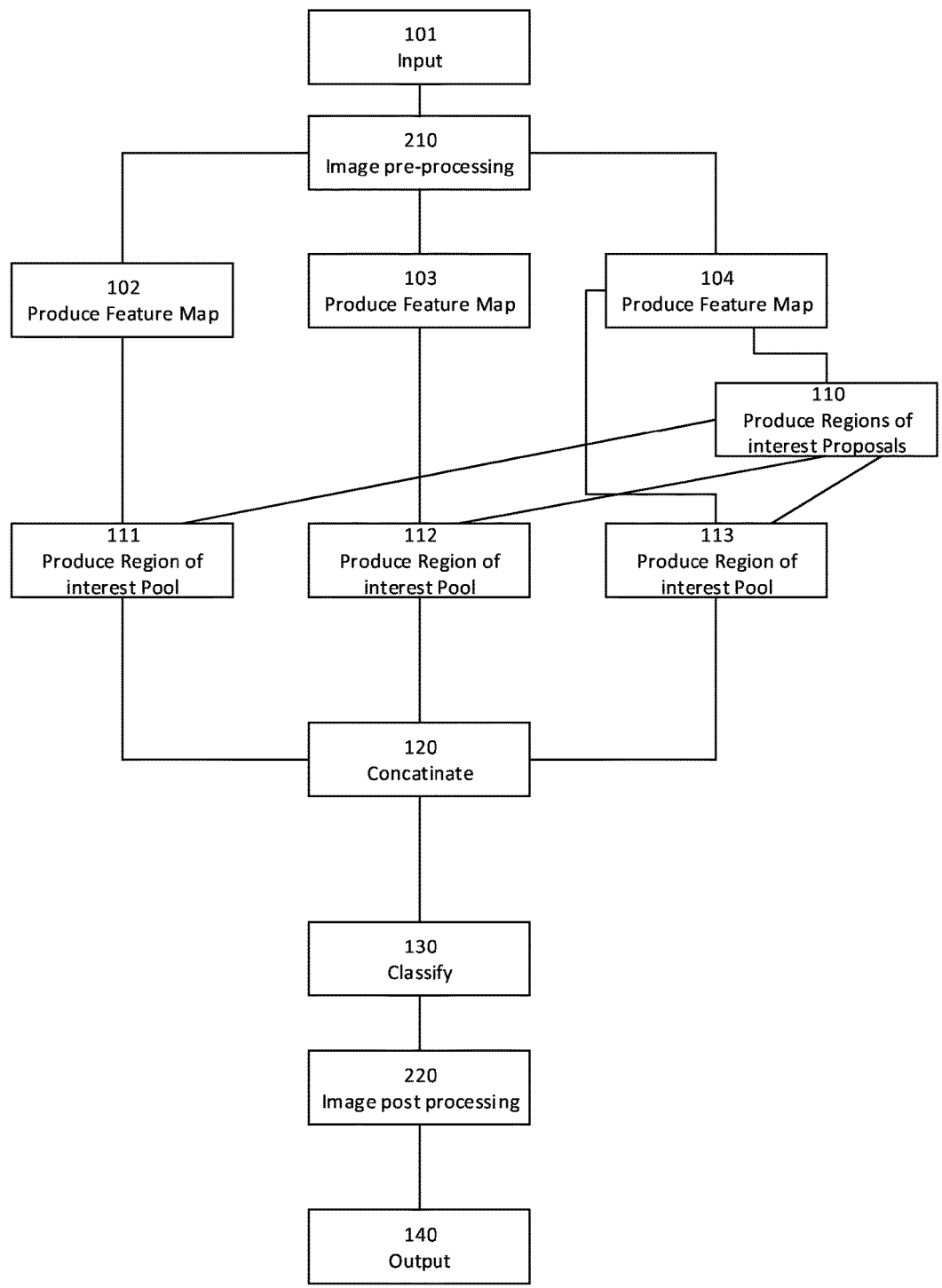
FIG. 5 is a flowchart schematically representing an optional flow of operations for processing an image with image pre-processing, according to some embodiments of the present invention.

Reference is now also made to FIG. 5, showing a flowchart schematically representing an optional flow of operations for processing an image with image pre-processing, according to some embodiments of the present invention. In such embodiments, after receiving the input image in 101, in 210 the image is pre-processed for the purpose of producing a modified image and for producing a plurality of visual attributes, for example lesion length. For example, when the input image is an image of a breast, in 210 the background and the pectoral muscle are optionally removed, leaving an image of only breast tissue. Optionally, one or more additional images are received. The one or more additional images may be captured by a model different from the model capturing the input image. For example, the input image may be captured by mammography and some of the one or more additional images may be captured by ultrasound. Optionally, when the input image is an image of a breast, a plurality of visual attributes may be produced by one or more of: extracting Fibro-glandular tissue from the input image and the one or more other images, extracting at least one saliency map of the only breast tissue image and the one or more other images, and producing a plurality of vessel identification by processing the only breast tissue image and the one or more other images. Optionally, in 210 the modified image is divided into a plurality of overlapping sub-images, and each sub-image is processed separately, starting with 102, 103 and 104, to produce the one or more classifications.

Optionally, after producing the one or more classifications, one or more bounding boxes of the one or more classifications are projected on the input image, and outputting the one or more classifications is optionally by outputting the one or more classifications projected on the input image. In addition, in some embodiments of the present invention the plurality of bounding boxes of the plurality of classifications are clustered according to redundant and overlapping bounding boxes, to ignore redundancies and overlaps. Optionally, the clustering is done by non-maximum suppression, where one or more classification with highest probability scores are selected and one or more classifications are suppressed, each of the one or more suppressed classifications having a bounding box significantly covered (for example, at least 75% or 80% covered) by a bounding box of a previously selected classification and a probability score lower than a probability score of the previously selected classification. Optionally, one or more remaining classifications after non-maximum suppression are projected on the input image before outputting the input image with projected classifications.

The present invention, in some embodiments thereof, proposes introducing additional input to the neural network, besides the input image, to improve detection, localization and classification of features in the input image. Introduction of additional input to the neural network may be done alternatively or in addition to producing a plurality of feature maps for producing one or more region of interest pools. In some embodiments, the system implements the following method.

Figure 6:
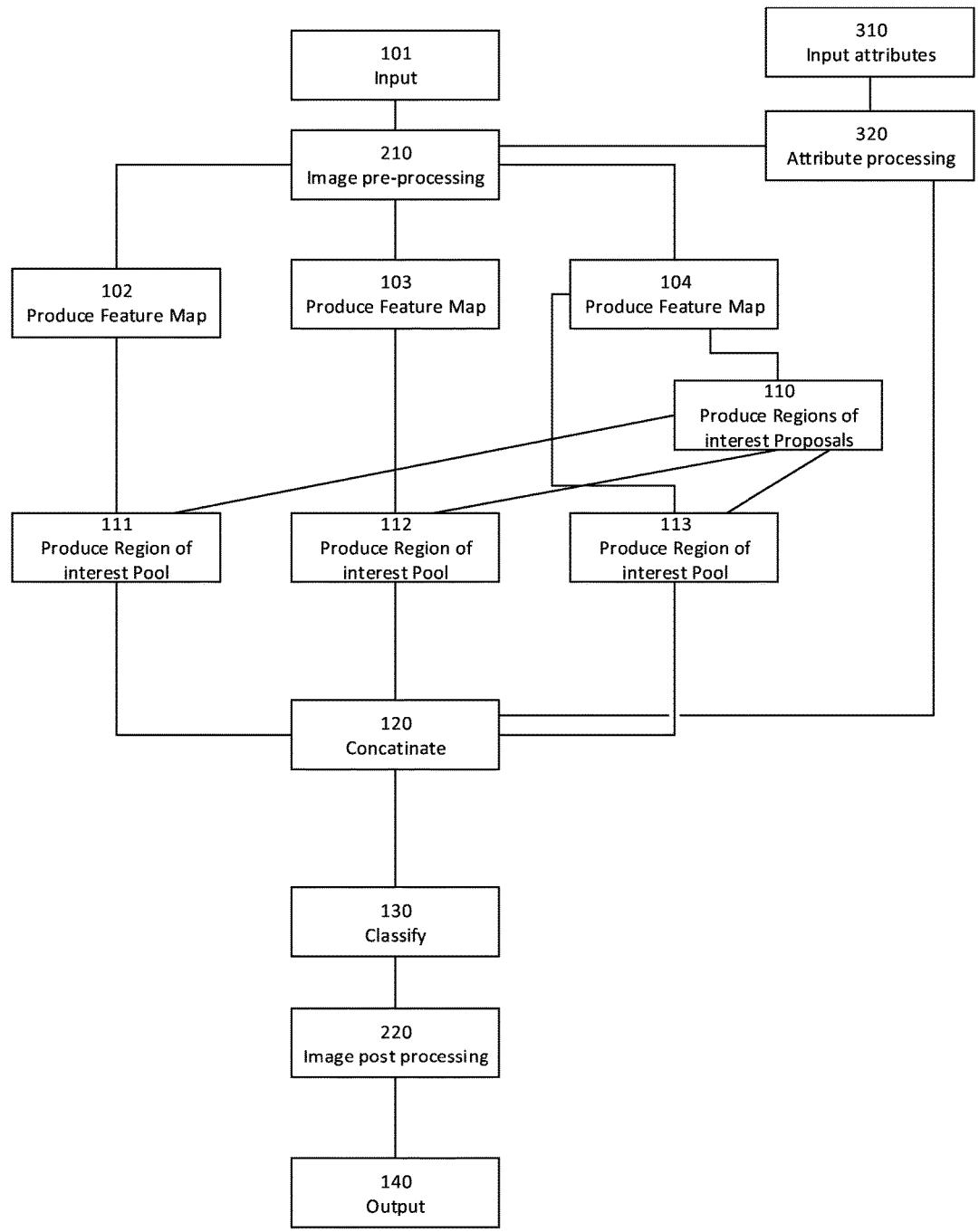
FIG. 6 is a flowchart schematically representing an optional flow of operations for processing an image with external attributes, according to some embodiments of the present invention.

Reference is now also made to FIG. 6, showing a flowchart schematically representing an optional flow of operations for processing an image with external attributes, according to some embodiments of the present invention. In such embodiments, the system receives in 310 a plurality of values of a plurality of attributes related to the input image. The plurality of attributes may comprise a plurality of clinical attributes obtained from sources other than the input image, for example a patient's age or a patient's family history. Optionally, the plurality of attributes comprises anatomical information such as a positive mask corresponding to a feature, for example Fibrograndular tissue, or a negative mask corresponding to a feature, for example a blood vessel. Optionally, the plurality of attributes comprises a plurality of visual attributes obtained in 210 from pre-processing the input image and a plurality of other input images. In 320, the system optionally processes the plurality of attributes values received in 310 and the plurality of visual attributes produced in 210. Optionally, processing in 310 is by another plurality of classification fully connected layer of the neural network, resulting in a plurality of processed values representing prior knowledge and expertise that might be lost by a fully automatic learning process. In some embodiments the plurality of processed values is combined in 120 with the plurality of deep layer region of interest pools produced in 111, 112 and 113, increasing the accuracy of the resulting combined region of interest pool.

Figure 7:
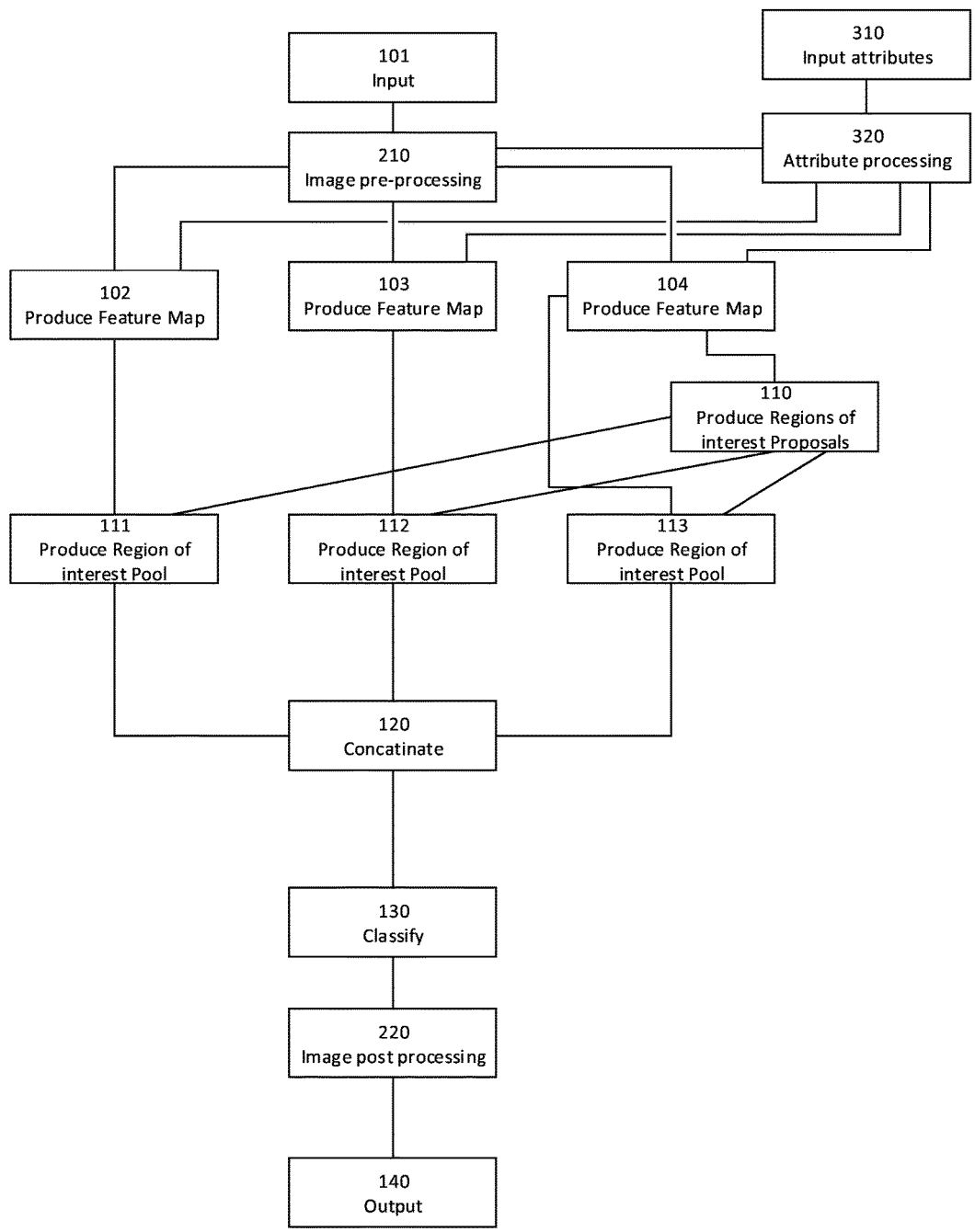
FIG. 7 is a flowchart schematically representing another optional flow of operations for processing an image with external attributes, according to some embodiments of the present invention.

In some other embodiments, the processed values of the plurality of attributes are used to modulate the neural network for producing the plurality of feature maps. Reference is now also made to FIG. 7, showing a flowchart schematically representing another optional flow of operations for processing an image with external attributes, according to some embodiments of the present invention. The plurality of processed values is used to modify a plurality of convolutional kernels of the first plurality of convolutional and pooling layers in 102, 103 and 104. For example, some of the plurality of convolution kernels may be chosen from one or more steerable filters in the plurality of processed values. Another example is using some other of the plurality of processed values as coefficients for some end-to-end basis filters in some of the first plurality of convolutional and pooling layers.

A key factor in successful detection, localization and classification of features by a neural network is the quality of training of the neural network. In some embodiments of the present invention, the system implements the following method to train the neural network, alternating between fine tuning for region proposals and object detection.

Figure 8:
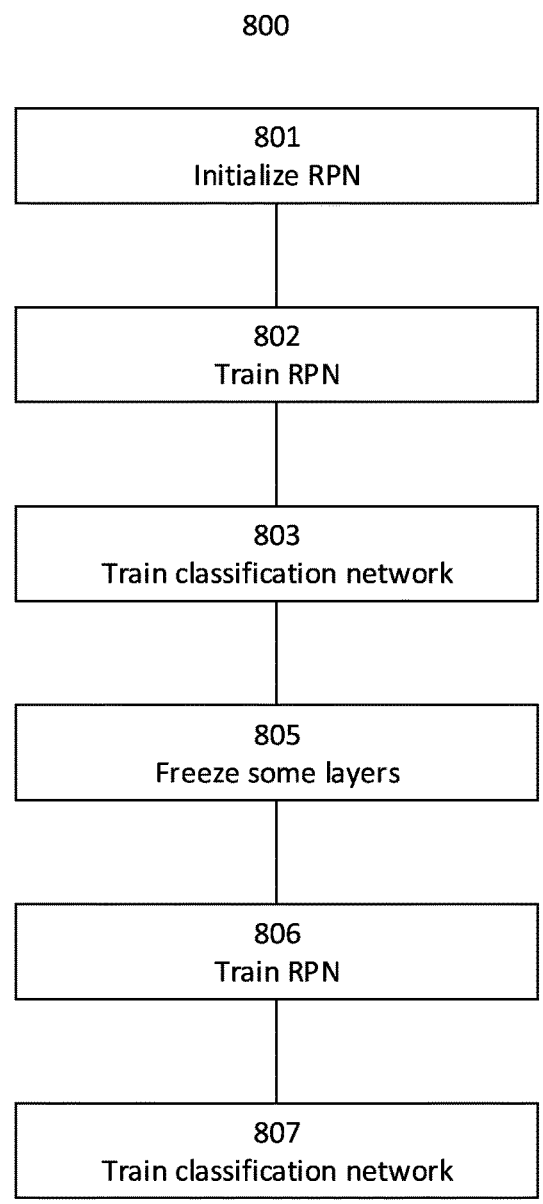
FIG. 8 is a flowchart schematically representing an optional flow of operations for training a neural network, according to some embodiments of the present invention.

Reference is now made to FIG. 8, showing a flowchart schematically representing an optional flow of operations for training a neural network, according to some embodiments of the present invention. In such embodiments, a region proposal network comprising a first plurality of layers of the neural network is initialized in 801 with an identified set of convolution weight values, obtained by training another neural network system on a large dataset of images by someone else. The other network may or may not implement the present invention. For example, the region proposal network may be initialized with a set of convolutional weight values obtained by training a network with ImageNet dataset of images. Next, in 802 the region proposal network is optionally trained by iteratively processing a plurality of identified images to produce a first set of convolution weights and a first plurality of region proposals. In 803, a classification network having a plurality of shared layers with the region proposal network by comprising the first plurality of layers is optionally trained by iteratively processing the first plurality of region proposals to produce a second set of convolution weight values. In 805 the first plurality of layers, shared between the region proposal network and the classification network, are optionally frozen. Freezing a layer means not changing the layer's weights during gradient descent and optimization in the iterative training process. Next, in 806 the region proposal network is optionally trained again by again iteratively processing the plurality of identified images by the regions proposal network having frozen layers, to produce a third set of convolution weight values and a second plurality of region proposals. In 807, the classification network is optionally trained again by iteratively processing the second plurality of region proposals to produce a third set of convolution weight values.

Some embodiments of the present invention may be used to assist one or more medical practitioners in diagnosing abnormal findings in one or more medical images. For example, the present invention may be used to assist a radiologist in sorting a plurality of medical images captured from a plurality of patients into a set of clean images displaying no abnormal findings and a set of images displaying at least one abnormal finding such as a lesion or a calcification. This allows a radiologist to concentrate only on the set of images displaying at least one abnormal finding. Another example is for a radiologist to compare, with regards to one or more images, a manual classification with one or more classifications produced by the system.

Some medical systems utilize an electronic record management (ERM) system, for storing and tracking medical records. In some embodiments of the present invention used in such a medical system, some of the medical records comprise one or more images. A system according to some embodiments of the present invention, stores a received image in the ERM system. Optionally, the ERM system comprises a database for storing the medical records. Optionally, the at least one processor retrieves the received image from the ERM system, in order to process the received image to detect and classify a plurality of findings in the received image. Optionally, the system initializes processing of every received image upon reception. Optionally, the system periodically scans all unscanned images received by the ERM system. Optionally, a person can instruct scanning of one or more received images.

Optionally, the one or more classifications are stored in the ERM system as projections marked on the received image. Optionally, the one or more classifications are stored in the ERM system as an extraction from the received image. Optionally the one or more classifications stored in the ERM system have a class label, a bounding box describing a locality within the received image and a probability score that a finding of the labeled class exists in the received image at the locality described by the bounding box. In some embodiments of the present invention the system issues an alert upon determining an abnormal finding in a received image. An abnormal finding may be determined by comparing the class label of the one or more classifications with a predefined set of abnormal classes, and by comparing the probability score of the one or more classifications with a threshold score value. When at least one classification of the one or more classifications has a class in the predefined set of abnormal classes and a probability score greater than the threshold score value, the system may determine an abnormal finding and optionally issue an alert to a person, for example a doctor. The received input image and the one or more classifications may be sent to the person. Optionally, the person instructs retrieval of the input image and the one or more classifications upon receiving an alert. Examples of alerts are a mail message, an immediate message and an indicator in an application.

Digital Imaging and Communications in Medicine (DICOM) is a standard for storing and transmitting medical images. DICOM includes at least one file format definition and at least one network communications protocol. In some embodiments of the present inventions the ERM stores the received image in a format compliant with DICOM's at least one file format definition. Optionally, the input image is received by the system via a network communications protocol compliant with DICOM's at least one network communications protocol. Optionally, the input image is sent to the person via the network communications protocol compliant with DICOM's at least one network communications protocol.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant input images and attributes will be developed and the scope of the terms "input images" and "attributes" are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for detection and classification of findings in an image, comprising:
    at least one hardware processor configured to:
        receive the image;
        process said image by a first plurality of convolutional and pooling layers of a neural network to produce a plurality of feature maps, each one of said plurality of feature maps comprising a plurality of location coordinates related to said image;
        process one of said plurality of feature maps by some of said first plurality of convolutional and pooling layers, a second plurality of convolutional and pooling layers and a first plurality of fully connected layers of said neural network to produce a plurality of region proposals;
        produce a plurality of region of interest (ROI) pools by using a third plurality of pooling layers of said neural network to downsample said plurality of region proposals with each one of said plurality of feature maps;
        process said plurality of ROI pools by at least one pool concatenation layer of said neural network to produce a combined ROI pool;
        process said combined ROI pool by a classification network comprising some other of said first plurality of convolutional and pooling layers to produce one or more classifications; and
        output said one or more classifications.

2. The system of claim 1, wherein said first plurality of convolutional and pooling layers comprises a plurality of layer blocks, each layer block comprising a sequence of convolutional and pooling layers;
    wherein said plurality of layer blocks are connected in a topology selected from a group consisting of a linear graph and a directed acyclic graph.

3. The system of claim 2, wherein said plurality of layer blocks of said first plurality of convolutional and pooling layers are connected linearly;
    wherein said first plurality of convolutional and pooling layers comprises a first sequence of layers consisting of: an input layer, followed by a first block consisting of a first sequence of convolutional and rectified linear unit layers, followed by a first pooling layer, followed by a second block consisting of a second sequence of convolutional and rectified linear unit layers, followed by a second pooling layer, followed by a third block consisting of a third sequence of convolutional and rectified linear unit layers, followed by a third pooling layer, followed by a fourth block consisting of a fourth sequence of convolutional and rectified linear unit layers, followed by a fourth pooling layer, and followed by a fifth block consisting of a fifth sequence of convolutional and rectified linear unit layers;
    wherein an output of said third sequence of convolutional and rectified linear unit layers is connected to a first normalized convolutional layer;
    wherein an output of said fourth sequence of convolutional and rectified linear unit layers is connected to a second normalized convolutional layer;
    wherein a first of said plurality of feature maps is produced by said first normalized convolutional layer;
    wherein a second of said plurality of feature maps is produced by said second normalized convolutional layer;
    wherein a third of said plurality of feature maps is produced by said fifth sequence of convolutional and rectified linear unit layers; and
    wherein said one of said plurality of feature maps is said third of said plurality of feature maps.

4. The system of claim 1, wherein each one of said plurality of region proposals comprises a boundary box, an object likelihood score and a non-object likelihood score.

5. The system of claim 1, wherein said third plurality of layers comprises a second sequence of layers consisting of: an ROI pooling layer, followed by a fifth pooling layer, followed by a fully connected layer and followed by a pooling reshaping layer.

6. The system of claim 1, wherein said classification network further comprises some of said first plurality of fully connected layers, a fourth plurality of fully connected layers, at least one bounding box regressor layer and one or more loss layers.

7. The system of claim 1, wherein said image is a medical image.

8. The system of claim 1, wherein said image is a medical image; and
    wherein said at least one hardware processor is further configured to:
        execute an electronic record management (ERM) system for storing a plurality of medical records comprising a plurality of medical images;
        store said image in said ERM system;
        retrieve said medical image from said ERM system before processing said image by said first plurality of convolutional and pooling layers; and
        store said one or more classifications in said ERM system.

9. The system of claim 8, wherein each one of said one or more classifications comprises a bounding box, a class and a probability score of said class at said bounding box; and
    wherein said at least one hardware processor is further configured to issue an alert upon determining said class of at least one of said one or more classifications is a member of a predetermined set of abnormal classes and said probability score of said at least one classification is greater than a threshold score value.

10. The system of claim 8, wherein said ERM system stores said image in a format compliant with Digital Imaging and Communications in Medicine (DICOM).

11. The system of claim 1, wherein said image is received by said at least one hardware processor via a network communications protocol compliant with DICOM.

12. A method for detection and classification of findings in an image, comprising:
receiving the image;
processing said image by a first plurality of convolutional and pooling layers of a neural network to produce a plurality of feature maps, each one of said plurality of feature maps comprising a plurality of location coordinates related to said image;
processing one of said plurality of feature maps by some of said first plurality of convolutional and pooling layers, a second plurality of convolutional and pooling layers and a first plurality of fully connected layers of said neural network to produce a plurality of region proposals;
producing a plurality of region of interest (ROI) pools by using a third plurality of pooling layers of said neural network to downsample said plurality of region proposals with each one of said plurality of feature maps;
processing said plurality of ROI pools by at least one pool concatenation layer of said neural network to produce a combined ROI pool;
processing said combined ROI pool by a classification network comprising some other of said first plurality of convolutional and pooling layers to produce one or more classifications; and
outputting said one or more classifications.

13. The method of claim 12, wherein said image is captured by a mammography of a breast; and
wherein said method further comprising:
after receiving said image:
removing background and pectoral muscle from said image to produce a breast tissue image;
receiving a plurality of other images;
producing a plurality of visual attributes by:
extracting Fibro-glandular tissue from said breast tissue image and said plurality of other images;
extracting at least one saliency map of said breast tissue image and said plurality of other images; and
processing said breast tissue image and said plurality of other images to produce a plurality of vessel identifications; and
dividing said breast tissue image into a plurality of overlapping sub-images; and
after producing said one or more classifications and before outputting said one or more classifications:
projecting one or more bounding boxes of said one or more classifications on said image.

14. The method of claim 12, further comprising after producing said one or more classifications and before outputting said one or more classifications:
clustering said one or more classifications according to redundant and overlapping bounding boxes to produce a one or more clustered classifications; and
projecting one or more bounding boxes of said clustered classifications on said image.

15. A system for detection and classification of findings in an image, comprising:
at least one hardware processor configured to:
receive the image;
receive a plurality of values of a plurality of attributes related to said image;
process said plurality of values by a first plurality of fully connected layers of a neural network to produce a plurality of processed values;
integrate said plurality of processed values into a plurality of layers of said neural network;
process said image by a first plurality of convolutional and pooling layers of a neural network to produce at least one feature map, each one of said at least one feature map comprising a plurality of location coordinates related to said image;
process one of said at least one feature map by some of said first plurality of convolutional and pooling layers, a second plurality of convolutional and pooling layers and a second plurality of fully connected layers of said neural network to produce a plurality of region proposals;
produce a plurality of region of interest (ROI) pools by using a third plurality of pooling layers of said neural network to downsample said plurality of region proposals with each one of said at least one feature map;
process said plurality of ROI pools by at least one pool concatenation layer to produce a combined ROI pool;
process said combined ROI pool by a classification network comprising some other of said first plurality of convolutional and pooling layers to produce one or more classifications; and
output said one or more classifications.

16. The system of claim 15, wherein said plurality of processed values is integrated into said plurality of layers by processing said plurality of processed values and said plurality of ROI pools by said least one pool concatenation layer to produce said combined ROI pool.

17. The system of claim 15, wherein said plurality of processed values is integrated into said plurality of layers by using said plurality of processed values as modulators for a plurality of convolutional kernels of said first plurality of convolutional and pooling layers before processing said image to produce said plurality of feature maps.

18. The system of claim 15, wherein said image is a medical image; and
wherein said plurality of attributes are selected from a group consisting of: a clinical record of a patient, a positive mask corresponding with an anatomical feature, a negative mask corresponding with an anatomical feature, a computed visual attribute, a density, a symmetry property, an additional view of said image, and a feature detected in another image.

19. The system of claim 18, wherein said medical image is captured by a mammography of a breast;
wherein said positive mask corresponds to Axilla tissue or Fibroglandular tissue; and
wherein said negative mask corresponds to a blood vessel.

20. The system of claim 18, wherein said medical image is captured by a method selected from a group consisting of: a computerized tomography of a brain, a magnetic resonance imaging of a brain, an ultrasound of a brain, a positron emission tomography of a brain and an X-ray radiography of a brain; and
wherein said positive mask corresponds to white matter.

* * * * *